(12) United States Patent
Chaimbault et al.

(10) Patent No.: US 8,691,854 B2
(45) Date of Patent: Apr. 8, 2014

(54) CHEMICAL COMPOUNDS AND THE USES THEREOF AS A MEDICINE

(75) Inventors: Corinne Chaimbault, Marseilles (FR); Cyrille Drouot, Draguignan (FR); Laure Jamot, Marseilles (FR); Rebecca Pruss, Cassis (FR); Céline Simon, Illkirch Graffenstaden (FR)

(73) Assignee: Trophos, Marseille Cedex 9 (FR)

( * ) Notice: Subject to any disclaimer, the term of this patent is extended or adjusted under 35 U.S.C. 154(b) by 824 days.

(21) Appl. No.: 11/994,354

(22) PCT Filed: Jun. 29, 2006

(86) PCT No.: PCT/FR2006/001521
§ 371 (c)(1),
(2), (4) Date: Aug. 21, 2008

(87) PCT Pub. No.: WO2007/003767
PCT Pub. Date: Jan. 11, 2007

(65) Prior Publication Data
US 2009/0203747 A1    Aug. 13, 2009

(30) Foreign Application Priority Data
Jul. 1, 2005 (FR) ..................... 05 07023

(51) Int. Cl.
*A01N 43/78* (2006.01)
*A61K 31/425* (2006.01)
*C07D 277/00* (2006.01)
*C07D 327/04* (2006.01)
*C07D 343/00* (2006.01)

(52) U.S. Cl.
USPC .............. 514/370; 548/190; 549/30

(58) Field of Classification Search
USPC .......... 514/370, 377, 386, 398; 548/190, 202, 548/233, 326.1; 549/30
See application file for complete search history.

(56) References Cited

PUBLICATIONS

Johne et. al., Pharmazie, 1979, Pharmazeutische Gesellschraft der DDR, vol. 34, issue 12, pp. 790-794 (Abstract).*
Boyd et. al., Journal of Medicinal Chemistry, 1999, American Chemical Society, vol. 42, pp. 5064-5071.*
Lin et. al., Bioorganic and Medicinal Chemistry Letters, 1999, Pergamon, vol. 9, pp. 2747-2752.*
Silberg et. al., CAS STN Abstract, 1965.*
Usol'tseva et. al., CAS STN Abstract, 1991.*
Carp et. al., CAS STN abstract of Analele Univ. Stiint., "Al. I. Cuza", publ. 1965.*
Usui et. al., Chemical Abstract Services (CAS) STN, publ. 1968.*

* cited by examiner

*Primary Examiner* — Sarah Pihonak
(74) *Attorney, Agent, or Firm* — Browdy and Neimark, PLLC

(57) ABSTRACT

The present invention relates to the field of pharmacy, especially the treatment of neurodegenerative diseases. The invention specifically relates to a family of chemical compounds for which a neuroprotective activity has been demonstrated. Given that certain members of said family are novel compounds which have never been described, the invention relates to said novel products, the synthesis method thereof and certain novel intermediate synthesis products.

The present invention further relates to compositions comprising the compounds of said family, and the use of said compounds as medicaments, especially for the preparation of a medicament for the treatment of neurodegenerative diseases.

18 Claims, No Drawings

CHEMICAL COMPOUNDS AND THE USES THEREOF AS A MEDICINE

The present invention relates to the field of pharmacy, particularly in the field of treatment of neurodegenerative diseases. More particularly, it relates to a family of chemical compounds for which neuroprotective activity was able to be demonstrated.

As certain members of said family are novel compounds never described, the invention relates to these novel products, to their synthesis method as well as to certain synthesis intermediates themselves novel compounds.

The present invention also relates to compositions comprising the compounds of the family, to the use of said compounds as drugs, particularly in the preparation of a drug intended for treating neurodegenerative diseases.

Neurodegenerative processes are characterized by dysfunction and death of the neurones causing the loss of neurological functions mediated by the brain, the spinal cord (central nervous system, CNS) and the peripheral nervous system (PNS). They may result i.a. from trauma, exposure to toxins, or pathological situations grouped under the term of neurodegenerative diseases or disorders.

Without pretending to be exhaustive, mention may be made among the most significant pathologies which are characterized by a degenerative process:
  hereditary or sporadic neurodegenerative chronic diseases, notably Alzheimer's disease (AD), Huntington's disease (HD), Parkinson's disease (PD), amyotrophic lateral sclerosis (ALS), spinal amyotrophies (SMA), Creutzfeldt-Jakob's disease, multiple sclerosis (MS), adrenoleucodystrophy, epilepsy, dementias, schizophrenia, neurological syndromes associated with the acquired immune deficiency syndrome (AIDS);
  neuronal lesions related to aging;
  hereditary or lesional peripheral neuropathies such as Fabry's, Charcot-Marie-Tooth's, Krabbe's diseases, leucodystrophies, diabetic neuropathies and those induced by anti-cancer treatments;
  traumas of the brain, of the peripheral nerves or the spinal cord;
  ischemias of the brain or spinal cord following a cerebrovascular stroke, or induced by a lack of blood irrigation;
  hereditary, lesional or age-related degenerations of sensorial neurones of vision, such as macular degenerations, pigmentary retinites, or degenerations of the optical nerve induced by glaucomas;
  hereditary, traumatic or age-related degenerations of sensorial neurones of hearing causing reduction or loss of hearing.

A large number of neurodegenerative diseases are characterized by the occurrence of mutations in certain proteins with the consequence of an alteration of the conformation of said proteins. These mutations are often responsible for a gain or a loss of one or more functions related to the expression of these mutated proteins.

Structural alteration of mutated proteins causes the formation of insoluble, ubiquitinated aggregates in affected cells as this was described for Parkinson's disease (PD), and for dementias with Lewy bodies, for Huntington's disease (HD), for spino-cerebral atrophy (SCA), for Kennedy's disease, or spino-bulbar muscular atrophy (SBMA), for amyotrophic lateral sclerosis (ALS), or outside of these cells as this was described for Alzheimer's disease (AD).

This description is more particularly correct for neurodegenerative diseases caused by expansion of CAG codons (coding for glutamine) in the coding or regulatory portion of a gene. Moreover in the text, these neurodegenerative diseases may be designated as "polyglutamine neuronal degenerations". Indeed, such mutations induce modifications of the protein interactions normally applied by the non-mutated protein; interactions which control neuronal activity in its entirety. Such diseases comprise but are not limited to:
  Huntington's disease, where multiple repetitions of "glutamine" codons (more than 36 repetitions) in the IT-15 gene coding for the huntingtin protein, causes the loss of neurones of the striatum and cortex,
  Kennedy's disease (or spino-bulbar muscular atrophy, SBMA) where multiple repetitions of "glutamine" codons (more than 40 codons) in the gene of the receptor for androgens, causes the loss of lumbar moto-neurones,
  spino-cerebral atrophy (SCA) of type I (or SCA-1)) where multiple repetitions of the glutamine amino acid (more than 41 amino acids) in ataxin-1, causes the loss of neurones from the cerebellum and the brain stem,
  Macchado-Joseph's disease (or SCA-3) where multiple repetitions of the glutamine amino acid (more than 68 amino acids) in the MJD-1 protein, causes the loss of neurones from the spinal cord and the cerebellum,
  SCA-6 where polymorphic repetitions of CAG are expressed in the alpha 1A voltage-dependent calcium channel,
  SCA-7 in which the mutation borne by ataxin-7 is associated with retinal degeneration in addition to cerebrospinal degeneration,
  dentato-rubro-pallido luysian atrophy (DRPA) where multiple repetitions of "glutamine" codons (more than 49 codons) in the coding portion of atrophin is the cause of loss of neurones from the globus pallidus and dentate-rubral and subthalamic nuclei.

Other spino-cerebral atrophies may further be mentioned, known as spino-cerebral heredodegenerations, characterized by a degeneration of the spinal cord and of other cerebral regions, such as for example,
  SCA-2, the mutation of which is borne on the chromosome 12,
  Friedreich's ataxia borne on the chromosome 9 with multiple repetitions of GAA codons within an intron, perturbing the expression of frataxin (a mitochondrial protein)
  ataxia with selective deficiency in vitamin E borne on chromosome 8, being expressed by a deficiency in alpha-TTP (Tocopherol Transfer Protein) (deficiency in vitamin E),
  myoclonic epilepsy with disparate fibers which is expressed by mutation of mitochondrial DNA,
  the syndrome of mitochondrial encephalopathy,
  telangiectasia ataxia borne on the chromosome 11 in the ATM gene and
  Nikali's juvenile cerebellar ataxia borne on the chromosome 10.

A therapeutic approach to the pathologies passes through neuroprotection, i.e. maintaining nerve cells in their natural physiological condition, or even restoration of a normal physiological condition in pathological nerve cells.

One of the therapeutic approaches for protecting neurones from death, as described in the prior art, is by providing neurotrophic proteins. These proteins, such as the neurotrophic factor derived from the brain (brain-derived neurotrophic factor, BDNF), the ciliary neurotrophic factor (CNTF), the nerve growth factor (NGF), the glia-derived neurotrophic factor (GDNF) are synthesized during embryo development or after a lesion in adults. These growth factors promote survival, maturation and differentiation of neuronal cells. Further, they inhibit apoptotic mechanisms, activate multiple survival routes and protect a large number of neurone populations.

The prior art therefore proposes the use of these growth factors in the treatment of most of neurone degenerations. But other routes are also described in the prior art, such as for example correction of early neurone dysfunctions by an action which does not imply trophic mimicry.

However and without denigrating the efforts of science to bring progress in the treatments of neurodegenerative diseases, there presently is no fully effective treatment for stopping neuronic degenerations, particularly polyglutamine neuronic degenerations.

All the neurodegenerative pathologies, in particular those described earlier, should respond to neuroprotective treatment administered at an early stage of the disease by a long-lasting improvement in the preserved neuronal functions and by reduction in the progression of the pathology.

The applicant, after long research, has demonstrated the therapeutic properties notably in treating or preventing neurodegenerative disorders, of chemical compounds fitting formula I, some of which are novel compounds.

Thus, the primary object of the invention is to provide novel chemical compounds having the following general formula I

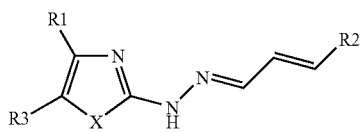

(I)

wherein

X represents a heteroatom selected from oxygen, sulfur or nitrogen, the nitrogen atom being possibly substituted with an alkyl group;

R1 and R2 represent an alkyl, cycloalkyl, aryl or heteroaryl group;

R3 represents a hydrogen atom or an alkyl or aryl group except for the compounds 3-phenyl-2-propenal-[4-(4-nitrophenyl)-2-thiazolyl]hydrazone;
3-phenyl-2-propenal-[4-(4-methoxyphenyl)-2-thiazolyl]hydrazone;
3-phenyl-2-propenal-[4-(4-fluorophenyl)-2-thiazolyl]hydrazone;
3-phenyl-2-propenal-[4-(4-bromophenyl)-2-thiazolyl]hydrazone;
3-phenyl-2-propenal-[4-(4-chlorophenyl)-2-thiazolyl]hydrazone;
3-phenyl-2-propenal-[4-(4-methylphenyl)-2-thiazolyl]hydrazone;
3-phenyl-2-propenal-[4-(1-naphthalenyl)-2-thiazolyl]hydrazone;
3-phenyl-2-propenal-(5-methyl-4-phenyl-2-thiazolyl)hydrazone;
3-phenyl-2-propenal-[4-(2,4-dichlorophenyl)-2-thiazolyl] hydrazone;
3-phenyl-2-propenal-[4-(3-nitrophenyl)-2-thiazolyl]hydrazone;
3-phenyl-2-propenal-[4-(1,1-dimethylethyl)-2-thiazolyl]hydrazone;
3-phenyl-2-propenal-[4-(4-chlorophenyl)-5-phenyl-2-thiazolyl]hydrazone;
2-butenal-[4-(4-nitrophenyl)-2-thiazolyl]hydrazone;
3-phenyl-2-propenal-[5-(4-chlorophenyl)-4-phenyl-2-thiazolyl]hydrazone;
3-(4-nitrophenyl)-2-propenal-(4,5-diphenyl-2-thiazolyl)hydrazone;
3-phenyl-2-propenal-(4,5-diphenyl-2-thiazolyl)hydrazone;
2-[[3-(3-nitrophenyl)-2-propenylidene]hydrazino]-4-thiazole carboxylic acid
2-[[3-(2-nitrophenyl)-2-propenylidene]hydrazino]-4-thiazole carboxylic acid
3-phenyl-2-propenal-[4-chloromethyl)-2-thiazolyl]hydrazone;
cinnamaldehyde-(4-phenyl-2-thiazolyl)hydrazone;
crotonaldehyde-(4-phenyl-2-thiazolyl)hydrazone;
2-furanacroleine-(4-methyl-2-thiazolyl)hydrazone,
cinnamaldehyde-(4-methyl-2-thiazolyl)hydrazone;

as well as their addition salts with pharmaceutically acceptable acids.

According to the invention, the addition salts with pharmaceutically acceptable acids may for example be salts formed with hydrochloric, hydrobromic, nitric, sulfuric, phosphoric, acetic, formic, propionic, benzoic, maleic, fumaric, succinic, tartaric, citric, oxalic, glyoxilic, aspartic, alkane-sulfonic acids, such as methane- or ethane-sulfonic acids, arylsulfonic acids, such as benzene- or paratoluene-sulfonic acids or carboxylic acids. Preferentially, according to the invention, the addition salts are hydrochloride, tartrate, methane-sulfonate.

According to the invention, is meant by an alkyl group, a carbon radical with 1 to 6 carbon atoms, either linear or branched, possibly substituted with a halogen atom, a hydroxyl radical, an amino group, a carboxylic acid group. By an either linear or branched carbon radical having 1 to 6 carbon atoms, is meant a radical selected from methyl, ethyl, propyl, isopropyl, butyl, isobutyl, sec-butyl, tert-butyl, pentyl, hexyl radicals. According to the invention, a preferred alkyl group is a methyl radical.

a cycloalkyl group, a radical derived from a saturated cyclic hydrocarbon radical having from 3 to 6 carbon atoms, optionally substituted with one or more halogen atoms, with one or more, either linear or branched, alkyl radicals having from 1 to 4 carbon atoms.

By a radical derived from a saturated cyclic hydrocarbon radical with 3 to 6 carbon atoms, is meant a radical selected from cyclopropyl, cyclobutyl, cyclopentyl, and cyclohexyl radicals. According to the invention, a preferred cycloalkyl group is a cyclohexyl radical.

an aryl group, a radical derived from a monocyclic or polycyclic aromatic group having from 6 to 10 carbon atoms, optionally substituted with one or more substituents. The substituants may be selected from a halogen atom, an alkyl group, either linear or branched, having from 1 to 4 carbon atoms, optionally substituted with one or more halogen atoms, with a hydroxyl group, with an amino group, or with an alkoxy group having from 1 to 3 carbon atoms, a hydroxyl group, a nitro group, a cyano group, a 1,3-dioxolyl group, a carbonyl group, a methylsulfonyl group or an amino group optionally mono- or di-substituted with an alkyl group having from 1 to 3 carbon atoms; preferentially according to the invention, the aryl group is a phenyl group optionally substituted as defined above;

a heteroaryl group, a monocyclic aromatic ring system which has five or six atoms, and containing one to two nitrogen atoms or one oxygen atom. Preferentially according to the invention, the preferred heteroaryl group is selected from pyrimidine and pyridine groups.

a carbonyl group, an aldehyde group, an alkylketone, an amide possibly substituted with a alkyl chain, carboxylic acid or alkyl ester.

According to a preferential embodiment of the invention, the compounds of formula I are those where X represents a sulfur atom.

According to another preferential embodiment of the invention, the compounds of formula I are those for which, everything being further identical with what was described earlier, R1 is a phenyl radical substituted in the para position with a chlorine atom, with a methyl or trifluoromethyl group, or in the meta position with a hydroxyl or a phenyl radical, disubstituted in ortho position with a methoxy group and in para position with a chlorine atom, or in ortho position with a methyl group and in para position with a hydroxyl group, or in meta position with a fluorine atom and in para with a chlorine atom.

According to another preferential embodiment of the invention, the compounds of formula I are those wherein, everything being further identical with what was described earlier, R2 is a pyridin-4-yl, pyridin-2-yl or pyridin-3-yl group, or a benzo[1,3]dioxol-5-yl group, or a phenyl group, or a phenyl group substituted in meta position with a nitro, cyano, methoxy, amino, methylsulfonyl, amide, methylketone, hydroxymethyl or hydroxyl group, or a phenyl group substituted in ortho position with a methoxy or a methyl group, or with a fluorine or chlorine atom, or a phenyl group substituted in para position with a fluorine atom.

According to another preferential embodiment of the invention, the compounds of formula I are those wherein, everything being further identical with what was described earlier, R3 is a hydrogen atom or a methyl group.

According to a more preferential embodiment of the invention, the compounds of formula I are those wherein X represents a sulfur atom, R3 is a hydrogen atom, R1 is a phenyl group substituted in the para position with a chlorine atom, a trifluoromethyl group, or in the meta position with a hydroxyl group, or a phenyl group, substituted in bothortho positions with a methoxy and in para with a chlorine atom, or substituted in both ortho position with a methyl group and in para with a hydroxyl group, or subtituted in both meta position with a fluorine atom and in para with a chlorine atom.

R2 is a pyridin-4-yl, pyridin-2-yl or pyridin-3-yl radical, or a benzo[1,3]dioxol-5-yle radical, or a phenyl group, or a phenyl group substituted in position meta with a nitro, cyano, amino, methylsulfone, amide, methylketone, hydroxymethyl, hydroxyl or methoxy group, or a phenyl group substituted in ortho position with a methoxy group, a methyl group, or a fluorine or a chlorine atom, or a phenyl group substituted in para position with a fluorine atom.

Thus, the preferred novel compounds according to the invention are:

3-(2-fluorophenyl)-2-propenal-[4-(4-chlorophenyl-2-thiazolyl)hydrazone;

3-(3-nitrophenyl)-2-propenal-[4-(4-chlorophenyl-2-thiazolyl)hydrazone;

3-(2-methoxyphenyl)-2-propenal-[4-(4-chlorophenyl-2-thiazolyl)hydrazone;

3-(3-methoxyphenyl)-2-propenal-[4-(4-chlorophenyl-2-thiazolyl)hydrazone;

3-phenyl-2-propenal-[4-(3-hydroxyphenyl-2-thiazolyl)hydrazone;

3-pyridin-4-yle-2-propenal-[4-(4-chlorophenyl-2-thiazolyl)hydrazone;

3-(2-méthylphenyl)-2-propenal-[4-(4-chlorophenyl-2-thiazolyl)hydrazone;

3-(3-cyanophenyl)-2-propenal-[4-(4-chlorophenyl-2-thiazolyl)hydrazone;

3-(2-chlorophenyl)-2-propenal-[4-(4-chlorophenyl-2-thiazolyl)hydrazone;

3-(3-aminophenyl)-2-propenal-[4-(4-chlorophenyl-2-thiazolyl)hydrazone;

3-(3-nitrophenyl)-2-propenal-[4-(4-trifluoromethylphenyl-2-thiazolyl) hydrazone;

3-((E)-3-{[4-(4-chlorophenyl)-thiazol-2-yl]-hydrazono}-propenyl)-phenol;

3-pyridin-4-yl-2-propenal-[4-(4-trifluoromethylphenyl-2-thiazolyl) hydrazone;

3-(3-aminophenyl)-2-propenal-[4-(4-trifluoromethylphényl-2-thiazolyl) hydrazone;

3-(3-methanesulfonylphenyl)-2-propenal-[4-(4-chlorophenyl-2-thiazolyl) hydrazone;

3-(3-cyanophenyl)-2-propenal-[4-(4-hydroxyphenyl-2-thiazolyl)hydrazone;

3-(3-benzo[1,3]dioxol-5-yl)-2-propenal-[4-(4-trifluoromethylphenyl-2-thiazolyl)hydrazone;

3-phenyl-2-propenal-[4-(4-chloro-2-methoxyphenyl-2-thiazolyl)hydrazone;

1-[3-((E)-3-{[4-(4-trifluoromethylphenyl)-thiazol-2-yl]-hydrazono}-propenyl)-phényl]-ethanone;

3-pyridin-2-yl-2-propenal-[4-(4-chlorophenyl-2-thiazolyl) hydrazone;

3-pyridin-2-yl-2-propenal-[4-(4-trifluoromethylphényl-2-thiazolyl) hydrazone;

3-méthyl-4-(2-{N'-[(E)-3-phenylprop-2-en-(E)-ylidene]-hydrazino}-thiazol-4-yl)-phénol;

[3-((E)-3-{[4-(4-trifluoromethylphenyl)-thiazol-2-yl]-hydrazono}-propenyl)-phényl]-methanol;

3-(4-fluorophenyl)-2-propenal-[4-(4-trifluoromethylphenyl-2-thiazolyl) hydrazone;

3-((E)-3-{[4-(4-trifluoromethylphenyl)-thiazol-2-yl]-hydrazono}-propenyl)-benzamide;

and most particularly 3-phenyl-2-propenal-[4-(4-trifluoromethylphenyl)-2-thiazolyl]hydrazone; 3-((E)-3-{[4-(4-trifluoromethylphenyl)-thiazol-2-yl]-hydrazono}-propenyl)-phenol; 3-(3-methanesulfonylphenyl)-2-propenal-[4-(4-trifluoromethylphenyl-2-thiazolyl)hydrazone; and 3-(3-cyanophenyl)-2-propenal-[4-(4-trifluoromethylphenyl-2-thiazolyl)hydrazone.

An object of the present invention is also methods for preparing the novel compounds of formula I.

According to a particular aspect of the invention, when the desired compound of formula I is a compound wherein X represents a sulfur atom, R1, R2 and R3 having the meanings described earlier, an object of the invention is a method wherein an α-bromo-ketone of formula II

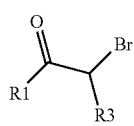

(II)

wherein R1 and R3 may have the meanings indicated earlier, is reacted with a compound of formula III,

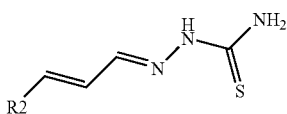
(III)

wherein R2 may have the meaning indicated earlier, in order to obtain the expected compound of formula I.

Under the preferential conditions for applying the method described above, the reaction of the compound of formula II with the compound of formula III is conducted in equimolar amounts
- in a minimum of suitable solvent, as absolute ethanol for example,
- at a temperature between 40 and 90° C., preferentially between 50 and 80° C. and for a period between 10 and 30 hours, preferentially between 15 and 20 hours.

The compounds of formula II are known and described derivatives (Tetrahedron 2003, 59(8), 1317-1325; JOC, 2003, 68(4), 1594-1596) and/or commercial derivatives.

Some compounds of formula III which are used as synthesis intermediates are novel. Thus, an object of the invention is also novel compounds of formula III wherein R2 may have the meanings indicated earlier, their use in chemical synthesis as well as their synthesis method, with the exception of the following compounds

[4-(2-formylvinyl)phenoxy]acetique thiosemicarbazone acid
4-(ethylsulfonyl)-cinnamaldehyde thiosemicarbazone
4-aminocinnamaldehyde thiosemicarbazone
4-ethoxycinnamaldehyde thiosemicarbazone
2-2-octenylidene-hydrazinecarbothioamide
2-[3-(2-furanyl)-2-propenylidene]-hydrazinecarbothioamide
2-[3-(4-pyridinyl)-2-propenylidene]-hydrazinecarbothioamide
cinnamaldehyde thiosemicarbazone
4-methylcinnamaldehyde thiosemicarbazone
2-chlorocinnamaldehyde thiosemicarbazone
4-chlorocinnamaldehyde thiosemicarbazone
4-isopropylcinnamaldehyde thiosemicarbazone
3,4-dimethoxy-2-methylcinnamaldehyde thiosemicarbazone
4-methoxycinnamaldehyde thiosemicarbazone
4-nitrocinnamaldehyde thiosemicarbazone
2-nitrocinnamaldehyde thiosemicarbazone
4-dimethylaminocinnalmaldehyde thiosemicarbazone
4-cyanocinnalmaldehyde thiosemicarbazone
crotonaldehyde thiosemicarbazone
2-nonenal thiosemicarbazone
2-heptenal thiosemicarbazone
2-hexenal thiosemicarbazone.

Said method for synthesizing compounds of formula III, is characterized in that a compound of formula IV

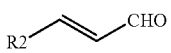
(IV)

wherein R2 may have the meanings indicated earlier, is reacted with thiosemicarbazide in order to obtain the novel expected compound of formula III.

Under the preferential conditions for applying the method described above, the reaction of the compound of formula IV is conducted in equimolar amounts of thiosemicarbazide in a minimum of suitable solvent such as anhydrous methanol refluxed for a period between 1 hour and 3 hours.

The compounds of formula IV are known, described (Org. Lett. 2003, 5(5) 777-780) and/or commercial derivatives.

According to another aspect, an object of the invention is compositions, notably pharmaceutical compositions or drugs, comprising at least one compound of formula I, with the exception of the following compounds 3-phenyl-2-propenal-[4-(4-nitrophenyl)-2-thiazolyl]hydrazone;
3-phenyl-2-propenal-[4-(4-methoxyphenyl)-2-thiazolyl]hydrazone;
3-phenyl-2-propenal-[4-(4-fluorophenyl)-2-thiazolyl]hydrazone;
3-phenyl-2-propenal-[4-(4-bromophenyl)-2-thiazolyl]hydrazone;
3-phenyl-2-propenal-[4-(4-chlorophenyl)-2-thiazolyl]hydrazone;
3-phenyl-2-propenal-[4-(4-methylphenyl)-2-thiazolyl]hydrazone;
3-phenyl-2-propenal-[4-(1-naphthalenyl)-2-thiazolyl]hydrazone;
3-phenyl-2-propenal-(5-methyl-4-phenyl-2-thiazolyl)hydrazone;
3-phenyl-2-propenal-[4-(2,4-dichlorophenyl)-2-thiazolyl]hydrazone;
3-phenyl-2-propenal-[4-(3-nitrophenyl)-2-thiazolyl]hydrazone;
3-phenyl-2-propenal-[4-(1,1-dimethylethyl)-2-thiazolyl]hydrazone;
3-phenyl-2-propenal-[4-(4-chlorophenyl)-5-phenyl-2-thiazolyl]hydrazone;
2-butenal-[4-(4-nitrophenyl)-2-thiazolyl]hydrazone;
3-phenyl-2-propenal-[5-(4-chlorophenyl)-4-phenyl-2-thiazolyl]hydrazone;
3-(4-nitrophenyl)-2-propenal-(4,5-diphenyl-2-thiazolyl)hydrazone;
3-phenyl-2-propenal-(4,5-diphenyl-2-thiazolyl)hydrazone;
2-[[3-(3-nitrophenyl)-2-propenylidene]hydrazino]-4-thiazole carboxylique acid
2-[[3-(2-nitrophenyl)-2-propenylidene]hydrazino]-4-thiazole carboxylique acid
3-phenyl-2-propenal-[4-chloromethyl)-2-thiazolyl]hydrazone;
cinnamaldehyde-(4-phenyl-2-thiazolyl)hydrazone;
crotonaldehyde-(4-phenyl-2-thiazolyl)hydrazone;
2-furanacroleine-(4-methyl-2-thiazolyl)hydrazone;
cinnamaldehyde-(4-methyl-2-thiazolyl)hydrazone;

as well as their addition salts with pharmaceutically acceptable acids.

The pharmaceutical compositions according to the invention may further comprise at least one other therapeutically active ingredient, for a simultaneous, separate or distributed use over time, notably when treating a subject affected with a neurodegenerative pathology.

The pharmaceutical compositions according to the invention may advantageously comprise one or more inert, i.e. pharmaceutically inactive and non-toxic, excipients or carriers. For example saline, physiological, isotonic, buffered solutions, etc., compatible with pharmaceutical use and known to one skilled in the art, may be mentioned. The compositions may contain one or more agents or carriers selected from dispersants, solubilizers, stabilizers, preservatives, etc. Agents or carriers which may be used in formulations (liquid and/or injectable and/or solid agents) are notably methylcellulose, hydroxymethylcellulose, carboxymethyl cellulose, cyclodextrins, polysorbate 80, mannitol, gelatin, lactose, vegetable or animal oils, acacia, etc. The compositions may be formulated as an injectable suspension, as gels, oils, tablets, suppositories, powders, gelatin capsules, capsules, etc., possibly by means of galenic forms or devices providing extended and/or delayed release. For this type of formulation, an agent such as cellulose, carbonates or starches, are used advantageously.

The amount of compound of formula I according to the invention, present in the therapeutical composition may be varied in order to obtain an active ingredient circulating rate required for obtaining the desired therapeutical effect for a particular patient, a composition, an administration method, and this without any toxicity for the patient.

The selected amount will depend on multiple factors, in particular on the administration route, on the administration time, on the moment of administration, on the elimination rate of the compound, of the different product(s) used in combination with the compound, on the age, the weight and the physical condition of the patient, as well as on his/her medical history, and on any other information known in medicine.

The prescription of the attending physician may start with doses less than those generally used, and these doses will then be gradually increased in order to better control the occurrence of possible secondary effects.

Generally, the daily dosage of the compound will be the minimum dose for obtaining the therapeutic effect. This dose will depend on different factors as mentioned earlier. The doses will generally be between 0.001 to 100 mg per kilo per day for humans, and preferentially from 0.001 to 10 mg per kilo and per day and even more advantageously from 0.01 to 1 mg per kilo and per day.

If required, the daily dose may be administered in two, three, four, five, six or more daily takings or by multiple sub-doses administered per suitable intervals during the day.

As indicated earlier, the applicant after a long research has demonstrated that chemical compounds represented by formula I, as well as their addition salts with pharmaceutically acceptable acids, have remarkable therapeutic properties, notably in treating or preventing neurodegenerative pathologies.

These properties are moreover illustrated in the experimental part. They justify the use of the compounds described above as well as of their additional salts with pharmaceutically acceptable acids, as a drug.

Accordingly and still according to another aspect, an object of the invention is also the use of the compounds of formula I.

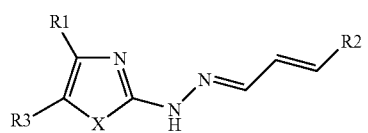
(I)

wherein X, R1, R2 and R3 may have the meanings described earlier, and
3-phenyl-2-propenal-[4-(4-nitrophenyl)-2-thiazolyl]hydrazone;
3-phenyl-2-propenal-[4-(4-methoxyphenyl)-2-thiazolyl]hydrazone;
3-phenyl-2-propenal-[4-(4-fluorophenyl)-2-thiazolyl]hydrazone;
3-phenyl-2-propenal-[4-(4-bromophenyl)-2-thiazolyl]hydrazone;
3-phenyl-2-propenal-[4-(4-chlorophenyl)-2-thiazolyl]hydrazone;
3-phenyl-2-propenal-[4-(4-methylphenyl)-2-thiazolyl]hydrazone;
3-phenyl-2-propenal-[4-(1-naphthalenyl)-2-thiazolyl]hydrazone;
3-phenyl-2-propenal-(5-methyl-4-phenyl-2-thiazolyl)hydrazone;
3-phenyl-2-propenal-[4-(2,4-dichlorophenyl)-2-thiazolyl]hydrazone;
3-phenyl-2-propenal-[4-(3-nitrophenyl)-2-thiazolyl]hydrazone;
3-phenyl-2-propenal-[4-(1,1-dimethylethyl)-2-thiazolyl]hydrazone;
3-phenyl-2-propenal-[4-(4-chlorophenyl)-5-phenyl-2-thiazolyl]hydrazone;
2-butenal-[4-(4-nitrophenyl)-2-thiazolyl]hydrazone;
3-phenyl-2-propenal-[5-(4-chlorophenyl)-4-phenyl-2-thiazolyl]hydrazone;
3-(4-nitrophenyl)-2-propenal-(4,5-diphenyl-2-thiazolyl)hydrazone;
3-phenyl-2-propenal-(4,5-diphenyl-2-thiazolyl)hydrazone;
2-[[3-(3-nitrophenyl)-2-propenylidene]hydrazino]-4-thiazole carboxylique acid
2-[[3-(2-nitrophenyl)-2-propenylidene]hydrazino]-4-thiazole carboxylique acid
3-phenyl-2-propenal-[4-chloromethyl)-2-thiazolyl]hydrazone;
cinnamaldehyde-(4-phenyl-2-thiazolyl)hydrazone;
crotonaldehyde-(4-phenyl-2-thiazolyl)hydrazone;
2-furanacroleine-(4-methyl-2-thiazolyl)hydrazone;
as a drug.

According to the invention,
3-(2-fluorophenyl)-2-propenal-[4-(4-chlorophenyl-2-thiazolyl)hydrazone;
3-(3-nitrophenyl)-2-propenal-[4-(4-chlorophenyl-2-thiazolyl)hydrazone;
3-(2-methoxyphenyl)-2-propenal-[4-(4-chlorophenyl-2-thiazolyl) hydrazone;
3-(3-methoxyphenyl)-2-propenal-[4-(4-chlorophenyl-2-thiazolyl) hydrazone;
3-phenyl-2-propenal-[4-(3-hydroxyphenyl-2-thiazolyl)hydrazone;
3-pyridin-4-yle-2-propenal-[4-(4-chlorophenyl-2-thiazolyl) hydrazone;
3-(2-methylphenyl)-2-propenal-[4-(4-chlorophenyl-2-thiazolyl)hydrazone;
3-(3-cyanophenyl)-2-propenal-[4-(4-chlorophenyl-2-thiazolyl)hydrazone;
3-(2-chlorophenyl)-2-propenal-[4-(4-chlorophenyl-2-thiazolyl)hydrazone;
3-(3-aminophenyl)-2-propenal-[4-(4-chlorophenyl-2-thiazolyl)hydrazone;
3-(3-nitrophenyl)-2-propenal-[4-(4-trifluoromethylphenyl-2-thiazolyl) hydrazone;
3-((E)-3-{[4-(4-chlorophenyl)-thiazol-2-yl]-hydrazono}-propenyl)-phenol;
3-pyridin-4-yl-2-propenal-[4-(4-trifluoromethylphenyl-2-thiazolyl) hydrazone;
3-(3-aminophenyl)-2-propenal-[4-(4-trifluoromethylphenyl-2-thiazolyl) hydrazone;
3-(3-methanesulfonylphenyl)-2-propenal-[4-(4-chlorophenyl-2-thiazolyl) hydrazone;
3-(3-cyanophenyl)-2-propenal-[4-(4-hydroxyphenyl-2-thiazolyl)hydrazone;
3-(3-benzo[1,3]dioxol-5-yl)-2-propenal-[4-(4-trifluoromethylphenyl-2-thiazolyl)hydrazone;
3-phenyl-2-propenal-[4-(4-chloro-2-methoxyphenyl-2-thiazolyl)hydrazone;

1-[3-((E)-3-{[4-(4-trifluoromethylphenyl)-thiazol-2-yl]-hydrazono}-propenyl)-phényl]-ethanone;
[3-pyridin-2-yl-2-propenal-[4-(4-chlorophenyl-2-thiazolyl) hydrazone;
3-pyridin-2-yl-2-propenal-[4-(4-trifluoromethylphenyl-2-thiazolyl) hydrazone;
3-methyl-4-(2-{N'-[(E)-3-phenylprop-2-en-(E)-ylidene]-hydrazino}-thiazol-4-yl)-phenol;
[3-((E)-3-{[4-(4-trifluoromethylphenyl)-thiazol-2-yl]-hydrazono}-propenyl)-phenyl]-methanol;
3-(4-fluorophenyl)-2-propenal-[4-(4-trifluoromethylphenyl-2-thiazolyl) hydrazone;
3-((E)-3-{[4-(4-trifluoromethylphenyl)-thiazol-2-yl]-hydrazono}-propenyl)-benzamide;

and most particularly 3-phenyl-2-propenal-[4-(4-trifluoromethylphenyl)-2-thiazolyl]hydrazone; 3-((E)-3-{[4-(4-trifluoromethylphenyl)-thiazol-2-yl]-hydrazono}-propenyl)-phenol; 3-(3-methanesulfonylphenyl)-2-propenal-[4-(4-trifluorométhylphenyl-2-thiazolyl)hydrazone; and 3-(3-cyanophenyl)-2-propenal-[4-(4-trifluoromethylphenyl-2-thiazolyl)hydrazone
are preferentially used as a drug.

According to still another aspect, an object of the invention is the use of the compounds of formula I, and
3-phenyl-2-propenal-[4-(4-nitrophenyl)-2-thiazolyl]hydrazone;
3-phenyl-2-propenal-[4-(4-methoxyphenyl)-2-thiazolyl]hydrazone;
3-phenyl-2-propenal-[4-(4-fluorophenyl)-2-thiazolyl]hydrazone;
3-phenyl-2-propenal-[4-(4-bromophenyl)-2-thiazolyl]hydrazone;
3-phenyl-2-propenal-[4-(4-chlorophenyl)-2-thiazolyl]hydrazone;
3-phenyl-2-propenal-[4-(4-methylphenyl)-2-thiazolyl]hydrazone;
3-phenyl-2-propenal-[4-(1-naphthalenyl)-2-thiazolyl]hydrazone;
3-phenyl-2-propenal-(5-méthyl-4-phenyl-2-thiazolyl)hydrazone;
3-phenyl-2-propenal-[4-(2,4-dichlorophenyl)-2-thiazolyl] hydrazone;
3-phenyl-2-propenal-[4-(3-nitrophenyl)-2-thiazolyl]hydrazone;
3-phenyl-2-propenal-[4-(1,1-dimethylethyl)-2-thiazolyl]hydrazone;
3-phenyl-2-propenal-[4-(4-chlorophenyl)-5-phenyl-2-thiazolyl]hydrazone;
2-butenal-[4-(4-nitrophenyl)-2-thiazolyl]hydrazone;
3-phenyl-2-propenal-[5-(4-chlorophenyl)-4-phenyl-2-thiazolyl]hydrazone;
3-(4-nitrophenyl)-2-propenal-(4,5-diphenyl-2-thiazolyl)hydrazone;
3-phenyl-2-propenal-(4,5-diphenyl-2-thiazolyl)hydrazone;
2-[[3-(3-nitrophenyl)-2-propenylidene]hydrazino]-4-thiazole carboxylique acid
2-[[3-(2-nitrophenyl)-2-propenylidene]hydrazino]-4-thiazole carboxylique acid
3-phenyl-2-propenal-[4-chloromethyl)-2-thiazolyl]hydrazone;
cinnamaldehyde-(4-phenyl-2-thiazolyl)hydrazone;
crotonaldehyde-(4-phenyl-2-thiazolyl)hydrazone;
2-furanacroleine-(4-methyl-2-thiazolyl)hydrazone;
cinnamaldehyde-(4-methyl-2-thiazolyl)hydrazone;
or of their addition salts with pharmaceutically acceptable acids, in the preparation of a pharmaceutical composition intended for treating neurodegenerative pathologies.

According to another aspect, an object of the invention is the use of the compounds of formula I, and
3-phenyl-2-propenal-[4-(4-nitrophenyl)-2-thiazolyl]hydrazone;
3-phenyl-2-propenal-[4-(4-methoxyphenyl)-2-thiazolyl]hydrazone;
3-phenyl-2-propenal-[4-(4-fluorophenyl)-2-thiazolyl]hydrazone;
3-phenyl-2-propenal-[4-(4-bromophenyl)-2-thiazolyl]hydrazone;
3-phenyl-2-propenal-[4-(4-chlorophenyl)-2-thiazolyl]hydrazone;
3-phenyl-2-propenal-[4-(4-methylphenyl)-2-thiazolyl]hydrazone;
3-phenyl-2-propenal-[4-(1-naphthalenyl)-2-thiazolyl]hydrazone;
3-phenyl-2-propenal-(5-methyl-4-phenyl-2-thiazolyl)hydrazone;
3-phenyl-2-propenal-[4-(2,4-dichlorophenyl)-2-thiazolyl] hydrazone;
3-phenyl-2-propenal-[4-(3-nitrophenyl)-2-thiazolyl]hydrazone;
3-phenyl-2-propenal-[4-(1,1-dimethylethyl)-2-thiazolyl]hydrazone;
3-phenyl-2-propenal-[4-(4-chlorophenyl)-5-phenyl-2-thiazolyl]hydrazone;
2-butenal-[4-(4-nitrophenyl)-2-thiazolyl]hydrazone;
3-phenyl-2-propenal-[5-(4-chlorophenyl)-4-phenyl-2-thiazolyl]hydrazone;
3-(4-nitrophenyl)-2-propenal-(4,5-diphenyl-2-thiazolyl)hydrazone;
3-phenyl-2-propenal-(4,5-diphenyl-2-thiazolyl)hydrazone;
2-[[3-(3-nitrophenyl)-2-propenylidene]hydrazino]-4-thiazole carboxylic acid
2-[[3-(2-nitrophenyl)-2-propenylidene]hydrazino]-4-thiazole carboxylic acid
3-phenyl-2-propenal-[4-chloromethyl)-2-thiazolyl]hydrazone;
cinnamaldehyde-(4-phenyl-2-thiazolyl)hydrazone;
crotonaldehyde-(4-phenyl-2-thiazolyl)hydrazone;
2-furanacroleine-(4-methyl-2-thiazolyl)hydrazone;
cinnamaldehyde-(4-methyl-2-thiazolyl)hydrazone;
or of their addition salts with pharmaceutically acceptable acids, in the preparation of a pharmaceutical composition intended for treating either hereditary or sporadic neurodegenerative chronic diseases, in particular polyglutamine neurodegenerative chronic diseases, more particularly Huntington's disease (HD).

Thus, the compounds according to the invention may be used in the preparation of pharmaceutical compositions, intended for the treatment of Alzheimer's disease (AD), Parkinson's disease (PD), spino-bulbar muscular atrophy or Kennedy's disease, dementias with Lewy bodies, spino-cerebeliar ataxia, amyotrophic lateral sclerosis (ALS), spinal amyotrophies (SMA), Creutzfeldt-Jakob's disease, multiple sclerosis (MS), adrenoleucodystrophy, epilepsy, dementias, schizophrenia, DRPA, neurological syndromes associated with the acquired immune deficiency syndrome (AIDS), neuronal lesions related to aging, hereditary or lesional peripheral neuropathies such Fabry's, Charcot-Marie-Tooth's, Krabbe's diseases, leucodystrophies, diabetic neuropathies and those induced by anti-cancer treatments, traumas of the brain, of the peripheral nerves or of the spinal cord, ischemias of the brain or the spinal cord following a cerebrovascular stroke, or induced by a lack of blood irrigation, hereditary, lesional degenerations or those related to aging of the sensorial neurones of vision, such as macular degenerations, pigmentary retinites, or degenerations of the optical nerve induced by glaucomas, hereditary, traumatic degenerations, or those related to the aging of hearing sensorial neurones causing a reduction or a loss of hearing.

Other aspects and advantages of the present invention will become apparent upon reading the examples which follow, which should be considered as illustrative, and non-limiting.

EXAMPLE 1

Synthesis of N3-(2-fluorophenyl)-2-propenal-[4-(4-chlorophenyl-2-thiazolyl)hydrazone Step 1A: Synthesis of 2-fluorocinnamaldehyde Thiosemicarbazone 390 mg (2.6 mmol) of 2-fluorocinnamaldehyde (Org. Lett. 5(5), 777-780, 2003) are solubilized in 10 ml of anhydrous methanol. 236 mg (2.6 mmol) of thiosemicarbazide are added. The reaction medium is heated and refluxed for 90 minutes.

The solution is cooled to room temperature, the formed precipitate is filtered.

250 mg of 2-fluorocinnamaldehyde thiosemicarbazone (yield: 43%) are thereby obtained.

Analysis:
$^1$H NMR: DMSO δ 11.45 (s, 1H), 8.21 (s, 1H), 7.90 (m, 1H), 7.67 (m, 2H), 7.36 (m, 1H), 7.25 (m, 2H), 7.02 (m, 2H).
LCMS [M+H]$^+$=225

Step 1B: Synthesis of 3-(2-fluorophenyl)-2-propenal-4-(4-chlorophenyl-2-thiazolyl)hydrazone 130 mg (0.5 mmol) of 2-bromo-4'-chloroacetophenone and 124 mg of 2-fluorocinnamaldehyde thiosemicarbazone prepared in step 1A are solubilized in 5 ml of absolute ethanol. The reaction medium is heated to 60° C. for 1 night.

The solution is cooled to room temperature. The product obtained after filtration is purified by flash chromatography. 90 mg of 3-(2-fluorophenyl)-2-propenal-[4-(4-chlorophenyl-2-thiazolyl)hydrazone (yield 50%) is thereby obtained.

Analysis:
$^1$H NMR: DMSO δ 12.2 (s, 1H), 7.83 (m, 3H), 7.81 (t, 1H), 7.47 (d, 2H), 7.40 (s, 1H), 7.36 (m, 1H), 7.23 (m, 2H), 7.04 (s, 2H)
LCMS [M+H]$^+$=356/358

EXAMPLE 2

Synthesis of 3-(3-nitrophenyl)-2-propenal-[4-(4-chlorophenyl-2-thiazolyl)hydrazone Step 2A: Synthesis of 3-nitrocinnamaldehyde Thiosemicarbazone The compound is prepared according to the method described in Example 1A from 3-nitrocinnamaldehyde (2.2 mmol) (Org. Lett. 5(5), 777-780, 2003) and from thiosemicarbazide (2.2 mmol). Yield 88%.

Analysis:
$^1$H NMR δ 11.45 (s, 1H), 8.36 (d, 1H), 8.28 (m, 1H), 8.14 (m, 1H), 8.01 (m, 1H), 7.92 (m, 1H), 7.67 (m, 2H), 7.22 (m, 1H), 7.04 (m, 1H).
LCMS [M+1]$^+$=251

Step 2B: Synthesis of 3-(3-nitrophenyl)-2-propenal-[4-(4-chlorophenyl-2-thiazolyl)hydrazone The compound is prepared according to the method described in Example 1B from 3-nitrocinnamaldehyde thiosemicarbazone (0.5 mmol) prepared in step 2A and from 2-bromo-4'-chloroacetophenone (0.5 mmol). Yield 53%.

Analysis:
$^1$H NMR: DMSO δ 12.26 (s, 1H), 8.40 (s, 1H), 8.11 (d, 2H), 7.91 (m, 3H), 7.66 (t, 1H), 7.47 (d, 2H), 7.42 (s, 1H), 7.23 (m, 1H), 7.12 (m, 1H).
LCMS [M+H]$^+$=384/386

EXAMPLE 3

Synthesis of 3-(2-methoxyphenyl)-2-propenal-[4-(4-chlorophenyl-2-thiazolyl)hydrazone Step 3A: Synthesis of 2-methoxycinnamaldehyde Thiosemicarbazone The compound is prepared according to the method described in Example 1A from 2-methoxycinnamaldehyde (6 mmol) and from thiosemicarbazide (6 mmol). Yield 45%.

Analysis:
$^1$H NMR: DMSO δ 11.32 (s, 1H), 8.14 (t, 1H), 7.87 (d, 1H), 7.60 (m, 1H), 7.52 (d, 1H), 7.32 (m, 1H), 7.12 (t, 2H), 6.95 (m, 3H), 3.85 (s, 3H).
LCMS [M+1]$^+$=237

Step 3B: Synthesis of 3-(2-methoxyphenyl)-2-propenal-[4-(4-chlorophenyl-2-thiazolyl)hydrazone The compound is prepared according to the method described in Example 1B from 2-methoxycinnamaldehyde thiosemicarbazone (0.5 mmol) prepared in step 3A and from 2-bromo-4'-chloroacetophenone (0.5 mmol). Yield 38%.

Analysis:
$^1$H NMR: DMSO δ 12.26 (s, 1H), 7.73 (d, 2H), 7.66 (m, 1H), 7.52 (d, 1H), 7.41 (m, 1H), 7.08 (s, 1H), 7.00 (m, 2H), 6.92 (m, 1H), 6.84 (s, 1H), 3.92 (s, 3H).
LCMS [M+H]$^+$=370/372

EXAMPLE 4

Synthesis of 3-phenyl-2-propenal-[4-(4-trifluoromethyl phenyl)-2-thiazolyl]hydrazone The compound is prepared according to the method described in Example 1B from cinnamaldehyde thiosemicarbazone (0.5 mmol) (Eur. J. Med. Chem. 25(7), 581-588, 1990) and from 2-bromo-4'-trifluoromethylacetophenone (0.5 mmol) (Tet., 59(8) 1317-1325, 2003). Yield 42%.

Analysis:
$^1$H NMR: DMSO δ 12.19 (s, 1H), 8.06 (d, 2H), 7.88 (d, 1H), 7.77 (d, 2H), 7.61 (d, 2H), 7.57 (s, 1H), 7.39 (m, 2H), 7.31 (m, 1H), 6.98 (m, 2H).
LCMS [M+H]$^+$=/374

EXAMPLE 5

Synthesis of 3-phenyl-2-propenal-[4-(4-chlorophenyl-5-methyl-2-thiazolyl)hydrazone The compound is prepared according to the method described in Example 1B from cinnamaldehyde thiosemicarbazone (0.12 mmol) (Eur. J. Med. Chem. 25(7), 581-588, 1990) and from 2-bromo-4'-chloropropiophenone (0.12 mmol) (J. Org. Chem. 68(4) 1594-1596, 2003). Yield 58%.

Analysis:
¹H NMR: DMSO δ 7.95 (d, 1H), 7.52 (m, 6H), 7.42 (m, 3H), 6.94 (m, 2H), 2.46 (s, 3H).
LCMS [M+H]⁺=/354/356

EXAMPLE 6

Synthesis of 3-(3-methoxyphenyl)-2-propenal-[4-(4-chlorophenyl-2-thiazolyl)hydrazone Step 6A: Synthesis of 3-methoxycinnamaldehyde Thiosemicarbazone The compound is prepared according to the method described in Example 1A from 3-methoxycinnamaldehyde (2.47 mmol) and from thiosemicarbazide (2.47 mmol). Yield 52%.
Analysis:
LCMS [M+1]⁺=237

Step 6B: Synthesis of 3-(3-methoxyphenyl)-2-propenal-[4-(4-chlorophenyl-2-thiazolyl)hydrazone The compound is prepared according to the method described in Example 1B from 3-methoxycinnamaldehyde thiosemicarbazone (0.52 mmol) prepared in step 6A and from 2-bromo-4'-chloroacetophenone (0.43 mmol). Yield 25%.
Analysis:
¹H NMR: DMSO δ 12.12 (s, 1H), 7.86 (m, 3H), 7.47 (d, 2H), 7.39 (s, 1H), 7.28 (t, 1H), 7.17 (m, 2H), 7.01 (m, 1H), 6.94 (s, 1H), 6.87 (m, 1H), 3.82 (s, 3H).
LCMS [M+H]⁺=370/372

EXAMPLE 7

Synthesis of 3-phenyl-2-propenal-[4-(3-hydroxyphenyl-2-thiazolyl)hydrazone

The compound is prepared according to the method described in Example 1B from cinnamaldehyde thiosemicarbazone (0.28 mmol) (Eur. J. Med. Chem. 25(7), 581-588, 1990) and from 2-bromo-4'-hydroxyacetophenone (0.46 mmol). Yield 28%.
¹H NMR: DMSO δ 12.07 (s, 1H), 945 (s, 1H), 7.87 (d, 1H), 7.61 (d, 2H), 7.38 (m, 2H), 7.32 (m, 3H), 7.25 (m, 2H), 6.97 (m, 2H), 6.71 (d, 1H).
LCMS [M+H]⁺=322

EXAMPLE 8

Synthesis of 3-pyridin-4-yl-2-propenal-[4-(4-chlorophenyl-2-thiazolyl)hydrazone

The compound is prepared according to the method described in Example 1B from 2-[3-(4-pyridinyl)-2-propenylidene]-hydrazinecarbothioamide (0.097 mmol) (Eur. J. Med. Chem., 1995, 30(12), 983-988) and from 2-bromo-4'-chloroacetophenone (0.097 mmol) Yield 45%.
¹H NMR: DMSO δ 12.30 (s, 1H), 8.54 (d, 2H), 7.86 (m, 3H), 7.56 (m, 2H), 7.47 (d, 2H), 7.42 (s, 1H), 7.35 (m, 1H), 6.94 (d, 1H)
LCMS [M+H]⁺=341/343 .

EXAMPLE 9

Synthesis of 3-(2-methylphenyl)-2-propenal-[4-(4-chlorophenyl-2-thiazolyl)hydrazone Step 9A: Synthesis of 2-methylcinnamaldehyde Thiosemicarbazone The compound is prepared according to the method described in Example 1A from 2-methylcinnamaldehyde (0.27 mmol) and from thiosemicarbazide (0.27 mmol). Yield 42%.
¹H NMR: DMSO δ 11.34 (s, 1H), 8.24 (t, 1H), 7.92 (d, 1H), 7.61 (m, 1H), 7.55 (m, 1H), 7.21 (m, 3H), 7.17 (m, 1H), 6.73 (m, 1H), 2.36 (s, 3H).
LCMS [M+1]⁺=220

Step 9B: Synthesis of 3-(2-methylphenyl)-2-propenal-[4-(4-chlorophenyl-2-thiazolyl)hydrazone The compound is prepared according to the method described in Example 1B from 2-methylcinnamaldehyde thiosemicarbazone (0.07 mmol) prepared in sept 9A and from 2-bromo-4'-chloroacetophenone (0.07 mmol). Yield 41%.
¹H NMR: DMSO δ 12.12 (s, 1H), 7.91 (d, 1H), 7.86 (d, 2H), 7.70 (m, 1H), 7.46 (d, 2H), 7.38 (s, 1H), 7.18 (m, 3H), 7.13 (s, 1H), 6.90 (m, 1H), 2.37 (s, 3H).
LCMS [M+H]⁺=354/356

EXAMPLE 10

Synthesis of 3-(3-cyanophenyl)-2-propenal-[4-(4-chlorophenyl-2-thiazolyl)hydrazone Step 10A: Synthesis of 3-cyanocinnamaldehyde Thiosemicarbazone The compound is prepared according to the method described in Example 1A from 3-cyanocinnamaldehyde (2.54 mmol) and from thiosemicarbazide (2.54 mmol). Yield 46%.
Analysis:
¹H NMR: 11.45 (s, 1H), 8.26 (d, 1H), 8.05 (s, 1H), 7.89 (m, 2H), 7.77 (m, 1H), 7.58 (m, 2H), 7.07 (m, 2H).
LCMS [M+1]⁺=231

Step 10B: Synthesis of 3-(3-cyanophenyl)-2-propenal-[4-(4-chlorophenyl-2-thiazolyl)hydrazone The compound is prepared according to the method described in Example 1B from 3-cyanocinnamaldehyde thiosemicarbazone (0.22 mmol) prepared in step 10A and from 2-bromo-4'-chloroacetophenone (0.22 mmol). Yield 51%.
Analysis:
LCMS [M+H]⁺=365/367

EXAMPLE 11

Synthesis of 3-(3-cyanophenyl)-2-propenal-[4-(4-trifluoromethylphenyl-2-thiazolyl)hydrazone The compound is prepared according to the method described in Example 1B from 3-cyanocinnamaldéhyde thiosemicarbazone (0.43 mmol) prepared in step 10A and from 2-bromo-4'-trifluoromethylacetophenone (0.43 mmol) (Tet., 59(8) 1317-1325, 2003). Yield 69%.
Analysis:
LCMS [M+H]+=399

EXAMPLE 12

Synthesis of 3-(2-chlorophenyl)-2-propenal-[4-(4-chlorophenyl-2-thiazolyl)hydrazone Step 12A: Synthesis of 2-chlorocinnamaldehyde Thiosemicarbazone The compound is prepared according to the method described in Example 1A from 2-chlorocinnamaldehyde (0.15 mmol) and from thiosemicarbazide (0.15 mmol). Yield 55%.
$^1$H NMR
LCMS [M+1]+=240/242

Step 12B: Synthesis of 3-(2-chlorophenyl)-2-propenal-[4-(4-chlorophenyl-2-thiazolyl)hydrazone The compound is prepared according to the method described in Example 1B from 2-chlorocinnamaldehyde thiosemicarbazone (0.08 mmol) prepared in step 12A and from 2-bromo-4'-chloroacetophenone (0.08 mmol). Yield 51%.
$^1$H NMR: DMSO δ 12.25 (s, 1H), 7.95 (m, 2H), 7.86 (m, 2H), 7.48 (m, 3H), 7.42 (s, 1H), 7.35 (m, 2H), 7.18 (d, 1H), 7.13 (d, 1H).
LCMS [M+H]+ 375/377

EXAMPLE 13

Synthesis of 3-(3-nitrophenyl)-2-propenal-[4-(4-trifluoromethyphenyl-2-thiazolyl)hydrazone The compound is prepared according to the method described in Example 1B from 3-nitrocinnamaldehyde thiosemicarbazone (0.5 mmoles) prepared in step 2A and from 2-bromo-4'-trifluoromethylacetophenone (0.05 mmoles). Yield 52%.
Analysis:
LCMS [M+H]+=419

EXAMPLE 14

Synthesis of 3-(3-aminophenyl)-2-propenal-[4-(4-chlorophenyl-2-thiazolyl)hydrazone Step 14A: Synthesis of 3-aminocinnamaldehyde Thiosemicarbazone A solution of 10 mL ethanol and 2 mL sodium carbonate 2N is saturated in hydrogen sulfur. 500 mg (2 mmoles) 3-nitrocinnamaldehyde thiosemicarbazone prepared in step 2A are added. The solution is heated 10 minutes at 50° C., then 3 minutes at 75° C. The solution is cooled in a ice bath. The crystals formed are filtered, washed with ethanol. 299 mg of 3-aminocinnamaldehyde thiosemicarbazone is obtained. Yield 68%.
Analysis:
LCMS [M+1]+=221

Step 14B: Synthesis of 3-(3-aminophenyl)-2-propenal-[4-(4-chlorophenyl-2-thiazolyl)hydrazone The compound is prepared according to the method described in example 1B from 3-aminocinnamaldehyde thiosemicarbazone (0.5 mmoles) prepared in step 14A and from 2-bromo-4'-chloroacetophenone (0.5 mmoles). Yield 53%.
Analysis:
RMN $^1$H: DMSO δ 7.73 (d, 2H), 7.46 (d, 1H), 7.40 (d, 2H), 7.16 (t, 1H), 6.8 (m, 3H), 6.67 (m, 1H), 6.52 (d, 1H), 6.48 (d, 1H).
LCMS [M+H]+=355/357

EXAMPLE 15

Synthesis of 3-((e)-3-{[4-(4-chlorophenyl)-thiazol-2-yl]-hydrazono}-propenyl)-phenol Step 15A: Synthesis of 3-hydroxycinnamaldehyde Thiosemicarbazone The compound is prepared according to the method described in example 1A from 3-hydroxycinnamaldehyde (6 mmoles) and from thiosemicarbazide (6 mmoles). Yield 28%.
Analysis:
LCMS [M+1]+=222

Step 15B: Synthesis of 3-((E)-3-{[4-(4-chlorophenyl)-thiazol-2-yl]-hydrazono}-propenyl)-phenol The compound is prepared according to the method described in example 1B from 3-hydroxycinnamaldehyde thiosemicarbazone (0.5 mmoles) prepared in step 15A and from 2-bromo-4'-chloroacetophenone (0.5 mmoles). Yield 39%.
Analysis:
RMN $^1$H: DMSO δ 12.10 (s, 1H), 9.47 (s, 1H), 7.85 (d, 3H), 7.46 (d, 2H), 7.38 (s, 1H), 7.16 (t, 1H), 7.03 (d, 1H), 6.92 (m, 1H), 6.85 (m, 3H), 6.70 (d, 1H).
LCMS [M+H]+=356/358

EXAMPLE 16

Synthesis of 3-pyridin-4-yl-2-propenal-[4-(4-trifluoromethylphenyl-2-thiazolyl)hydrazone The compound is prepared according to the method described in example 1B from 2-[3-(4-pyridinyl)-2-propenylidene]-hydrazinecarbothioamide (0.097 mmoles) (Eur. J. Med. Chem., 1995, 30(12), 983-988) and from 2-bromo-4'-trifluoromethylacetophenone (0.097 mmoles) Yield 45%.
RMN $^1$H: DMSO δ 12.36 (s, 1H), 8.54 (d, 2H), 8.06 (m, 2H), 7.90 (d, 1H), 7.78 (d, 2H), 7.57 (m, 3H), 7.25 (m, 1H), 6.94 (d, 1H).
LCMS [M+H]+=375

EXAMPLE 17

Synthesis of 3-(3-aminophenyl)-2-propenal-[4-(4-trifluoromethylphenyl-2-thiazolyl)hydrazone The compound is prepared according to the method described in example 1B from 3-aminocinnamaldehyde thiosemicarbazone (0.5 mmoles) prepared in step 14A and from 2-bromo-4'-trifluoromethylacetophenone (0.5 mmoles). Yield 58%.
Analysis:
LCMS [M+H]+=389

EXAMPLE 18

Synthesis of 3-(3-methanesulfonylphenyl)-2-propenal-[4-(4-chlorophenyl-2-thiazolyl)hydrazone

Step 18A: Synthesis of 3-methylsulfonylcinnamaldehyde Thiosemicarbazone

The compound is prepared according to the method described in example 1A from 3-methylsulfonylcinnamaldehyde (3.8 mmoles) and from thiosemicarbazide (3.8 mmoles). Yield 70%.
Analysis:
LCMS [M+1]$^+$=284

Step 18B: Synthesis of 3-(3-methanesulfonylphenyl)-2-propenal-[4-(4-chlorophenyl-2-thiazolyl)hydrazone The compound is prepared according to the method described in example 1B from 4-méthylsulfonylcinnamaldehyde thiosemicarbazone (2.68 mmoles) prepared in step 18A and from 2-bromo-4'-chloroacetophenone (2.68 mmoles). Yield 60%.
Analysis:
RMN $^1$H: DMSO δ 12.05 (s, 1H), 8.21 (s, 1H), 7.99 (m, 1H), 7.88 (m, 3H), 7.78 (m, 1H), 7.52 (m, 1H), 7.41 (m, 2H), 7.30 (m, 1H), 7.18 (m, 1H), 7.01 (m, 1H), 3.34 (s, 3H).
LCMS [M+H]$^+$=418/420

EXAMPLE 19

Synthesis of 3-(3-cyanophenyl)-2-propenal-[4-(3-hydroxyphenyl-2-thiazolyl)hydrazone The compound is prepared according to the method described in example 1B from 3-cyanocinnamaldehyde thiosemicarbazone (0.22 mmoles) prepared in step 10A and from 2-bromo-3'-hydroxyacetophenone (0.22 mmoles). Yield 51%.
Analysis:
RMN $^1$H: DMSO δ 12.10 (s, 1H), 9.45 (s, 1H), 8.11 (s, 1H), 7.90 (d, 1H), 7.78 (d, 1H), 7.67 (m, 1H), 7.56 (m, 1H), 7.25 (m, 3H), 7.18 (t, 2H), 6.98 (d, 1H), 6.68 (d, 1H).
LCMS [M+H]$^+$=347

EXAMPLE 20

Synthesis of 3-((E)-3-{[4-(4-trifluoromethylphenyl)-thiazol-2-yl]-hydrazono}-propenyl)-phenol The compound is prepared according to the method described in example 1B from 3-hydroxycinnamaldehyde thiosemicarbazone (0.5 mmoles) prepared in step 15A and from 2-bromo-4'-trifluoromethylacétophenone (0.5 mmoles). Yield 31%.
Analysis:
RMN $^1$H: DMSO δ 12.15 (s, 1H), 9.48 (s, 1H), 8.06 (d, 2H), 7.85 (d, 1H), 7.76 (d, 2H), 7.56 (s, 1H), 7.16 (t, 1H), 7.04 (d, 1H), 6.92 (m, 1H), 6.72 (m, 2H), 6.70 (d, 1H).
LCMS [M+H]$^+$=390

EXAMPLE 21

Synthesis of 3-(3-benzo[1,3]dioxol-5-yl)-2-propenal-[4-(4-trifluoromethylphenyl-2-thiazolyl)hydrazone

Step 21A: Synthesis of (3-benzo[1,3-dioxol-5-yl)-propenal thiosemicarbazone

The compound is prepared according to the method described in example 1A from 2-(3-benzo[1,3]dioxol-5-yl)-propenal (0.15 mmoles) and from thiosemicarbazide (0.15 mmoles). Yield 51%.
LCMS [M+1]$^+$=250

Step 21B: Synthesis of 3-(3-benzo[1,3-dioxol-5-yl)-2-propenal-[4-(4-trifluoromethylphenyl-2-thiazolyl) hydrazone The compound is prepared according to the method described in example 1B from (3-benzo[1,3]dioxol-5-yl)-propenal thiosemicarbazone (0.08 mmoles) prepared in step 21A and from 2-bromo-4'-trifluoromethylacetophenone (0.08 mmoles). Yield 51%.
RMN $^1$H: DMSO δ 12.20 (s, 1H), 8.06 (m, 2H), 7.76 (m, 2H), 7.68 (m, 2H), 7.54 (s, 1H), 7.32 (s, 1H), 6.92 (d, 1H), 6.87 (m, 2H), 6.04 (s, 2H).
LCMS [M+H]$^+$=418

EXAMPLE 22

Synthesis of 3-phenyl-2-propenal-[4-(4-chloro-2-methoxyphenyl-2-thiazolyl)hydrazone The compound is prepared according to a method described in example 1B from cinnamaldehyde thiosemicarbazone (0.28 mmoles) (Eur. J. Med. Chem. 25(7), 581-588, 1990) and from 2-bromo-4'-chloro-2'-methoxyacetophenone (0.28 mmoles). Yield 36%.
RMN $^1$H: DMSO δ 12.06 (s, 1H), 8.06 (d, 1H), 7.87 (d, 1H), 7.61 (d, 2H), 7.38 (m, 3H), 7.28 (m, 1H), 7.17 (s, 1H), 7.07 (m, 1H), 6.98 (m, 2H), 3.94 (s, 3H).
LCMS [M+H]$^+$=370/372

EXAMPLE 23

Synthesis of 3-((e)-3-{[4-(4-trifluoromethyl phenyl)-thiazol-2-yl]-hydrazono}-propenyl)-benzamide

Step 23A: Synthesis of 3-((E)-3-thiosemicarbazone-propenyl)-benzamide

The compound is prepared according to the method described in example 1A from 3-((E)-oxopropenyl)-benzamide (0.15 mmoles) and from thiosemicarbazide (0.15 mmoles). Yield 41%.
LCMS [M+1]$^+$=249

Step 23B: Synthesis of 3-((E)-3-{[4-(4-trifluoromethylphenyl)-thiazol-2-yl]-hydrazono}-propenyl)-benzamide The compound is prepared according to the method described in example 1B from 3-((E)-3-thiosemicarbazonepropenyl)-benzamide (0.08 mmoles) prepared in step 23A and from 2-bromo-4'-trifluoromethylacetophenone (0.08 mmoles). Yield 51%.

RMN $^1$H: DMSO δ 12.22 (s, 1H), 8.15 (s, 1H), 8.06 (d, 3H), 7.90 (d, 1H), 7.78 (m, 3H), 7.70 (m, 1H), 7.57 (s, 1H), 7.46 (m, 2H), 7.14 (m, 1H), 7.00 (d, 1H).

LCMS [M+H]$^+$=417

EXAMPLE 24

Synthesis of 3-(3-methanesulfonylphenyl)-2-propenal-[4-(4-trifluoromethylphenyl-2-thiazolyl)hydrazone The compound is prepared according to the method described in example 1B from 4-methylsulfonylcinnamaldehyde thiosemicarbazone (2.95 mmoles) prepared in step 18A and from 2-bromo-4'-trifluoromethylacetophenone (2.95 mmoles). Yield 73%.

Analysis:

RMN $^1$H: DMSO δ 12.29 (s, 1H), 8.14 (s, 1H), 8.05 (d, 2H), 7.97 (m, 2H), 7.78 (m, 3H), 7.63 (m, 1H), 7.58 (m, 1H), 7.24 (m, 1H), 7.09 (m, 1H), 3.31 (s, 3H).

LCMS [M+H]$^+$=452

EXAMPLE 25

Synthesis of 3-pyridin-2-yl-2-propenal-[4-(4-chlorophenyl-2-thiazolyl)hydrazone

Step 25A: Synthesis of 2-[3-(2-pyridinyl)-2-propenylidene]-hydrazine carbothioamide The compound is prepared according to the method described in example 1A from (E)-3-pyridin-2-yl-propenal (0.2 mmoles) and from thiosemicarbazide (0.2 mmoles). Yield 43%.

LCMS [M+1]$^+$=207

Step 25B: Synthesis of 3-pyridin-2-yl-2-propenal-[4-(4-chlorophenyl-2-thiazolyl)hydrazone The compound Is prepared according to the method described in example 1B from 2-[3-(2-pyridinyl)-2-propenylidene]-hydrazinecarbothioamide (0.097 m moles) and from 2-bromo-4'-chloroacetophenone (0.097 mmoles) Yield 41%.

RMN $^1$H: DMSO δ 12.30 (s, 1H), 8.58 (m, 1H), 7.90 (m, 1H), 7.87 (m, 2H), 7.78 (m, 1H), 7.59 (d, 1H), 7.46 (d, 2H), 7.41 (s, 1H), 7.30 (m, 2H), 6.98 (d, 1H).

LCMS [M+H]$^+$=341/343

EXAMPLE 26

Synthesis of 3-pyridin-2-yl-2-propenal-[4-(4-trifluoromethylphenyl-2-thiazolyl)hydrazone The compound is prepared according to the method described in example 1B from 2-[3-(2-pyridinyl)-2-propenylidene]-hydrazinecarbothioamide prepared in step 25A (0.11 mmoles) and from 2-bromo-4'-trifluoromethylacetophenone (0.11 mmoles) Yield 46%.

RMN $^1$H: DMSO δ 12.30 (s, 1H), 8.58 (m, 1H), 8.07 (d, 2H), 7.92 (d, 1H), 7.77 (m, 8H), 7.59 (m, 2H), 7.30 (m, 2H), 7.00 (d, 1H).

LCMS [M+H]$^+$=375

EXAMPLE 27

Synthesis of 3-methyl-4-(2-{N'-[(E)-3-phenylprop-2-en-(E)-ylidene]-hydrazino}-thiazol-4-yl)-phenol The compound is prepared according to the method described in example 1B from cinnamaldehyde thiosemicarbazone (0.28 mmoles) (Eur. J. Med. Chem. 25(7), 581-588, 1990) and from 2-bromo-4'-hydroxy-2'-methylacetophenone (0.28 mmoles). Yield 36%.

RMN $^1$H: DMSO δ 11.85 (s, 1H), 9.42 (s, 1H), 7.82 (d, 1H), 7.64 (d, 2H), 7.36 (m, 3H), 7.31 (m, 1H), 6.92 (m, 2H), 6.66 (s, 1H), 6.63 (m, 2H), 2.35 (s, 3H).

LCMS [M+H]$^+$=336

EXAMPLE 28

Synthesis of [3-((E)-3-{[4-(4-trifluoromethylphenyl)-thiazol-2-yl]-hydrazono}-propenyl)-phenyl]-methanol Step 28A: Synthesis of 3-hydroxymethylcinnamaldehyde Thiosemicarbazone The compound is prepared according to the method described in example 1A from 3-hydroxymethylcinnamaldehyde (3 mmoles) et de thiosemicarbazide (3 mmoles). Yield 25%.

Analysis:

LCMS [M+1]$^+$=236

Step 28B: Synthesis of [3-((E)-3-{[4-(4-trifluoromethylphenyl)-thiazol-2-yl]-hydrazono}-propenyl)-phenyl]-methanol The compound is prepared according to the method described in example 1B from 3-hydroxymethylcinnamaldehyde thiosemicarbazone (0.4 mmoles) prepared in step 28A and from 2-bromo-4'-trifluoromethylacetophenone (0.4 mmoles). Yield 37%.

Analysis:

RMN $^1$H: DMSO δ 12.18 (s, 1H), 8.05 (m, 2H), 7.88 (m, 1H), 7.76 (d, 2H), 7.54 (m, 2H), 7.48 (m, 1H), 7.33 (t, 1H), 7.25 (m, 1H), 6.96 (m, 2H), 5.21 (m, 1H), 4.52 (m, 2H).

LCMS [M+H]$^+$=404

EXAMPLE 29

Synthesis of 3-(4-fluorophenyl)-2-propenal-[4-(4-trifluoromethylphenyl-2-thiazolyl)hydrazone Step 29A: Synthesis of 4-fluorocinnamaldehyde Thiosemicarbazone The compound is prepared according to the method described in example 1A from 4-fluorocinnamaldehyde (1.5 mmoles) and from thiosemicarbazide (1.5 mmoles). Yield 53%.

Analysis:

LCMS [M+1]$^+$=224

Step 29B: Synthesis of 3-(4-fluorophenyl)-2-propenal-[4-(4-trifluoromethylphenyl 2-thiazolyl)hydrazone The compound is prepared according to the method described in example 1B from 4-fluorocinnamaldehyde thiosemicarbazone (0.3 mmoles) prepared in step 29A and from 2-bromo-4'-trifluoromethylacetophenone (0.3 mmoles). Yield 46%.

Analysis:
RMN $^1$H: DMSO δ 12.18 (s, 1H), 8.05 (d, 2H), 7.86 (m, 1H), 7.77 (m, 2H), 7.68 (m, 2H), 7.56 (s, 1H), 7.21 (t, 2H), 6.96 (m, 2H).

LCMS [M+H]$^+$=392

Pharmacological Study

In order to demonstrate the neuroprotective properties of the compounds of formula I according to the invention, the applicant studied their activity in an in vitro model of expression of huntingtin which has mutated in primary neurones isolated from rat striatum. This model mimics the degeneration conditions of Huntington's disease. With it, it is therefore possible to identify molecules which combine several of the action mechanisms described earlier for reducing the dysfunction preceding neuronal death and promoting survival of dysfunctional neurones.

EXAMPLE 30

Evaluation of the Protection Provided by the Compound of Formula I on Striatum Neurones in a Death Test Induced by Over-Expression of a Mutated Form of Huntingtine by Using GFP as Reporter Gene All the molecular biologic techniques used in this example are standard techniques of the field, perfectly known to one skilled in the art and which may be found in any book relating to said techniques.

Primary cultures of striatum neurones are prepared as described in the literature (Mao L. et al., Methods Mol. Med., 2003, 79: 379-86).

Before sowing, an expression vector containing a promoter element followed by the DNA coding for a truncated form of huntingtin which comprises the first 480 amino acids and 68 CAG codons (Saudou et al., Cell, 1998, 95:55-66), purified beforehand, is introduced by electroporation according to the procedure described by Raoul et al., (Neuron, 2002, 35:1067-83).

A second expression vector, also purified beforehand, containing DNA coding for the green fluorescent protein (GFP) (Columbia University) is also electroporated and is used as a reporter gene.

The cells which survive electroporation are sown at a density of 4,000 cells per well on 96-well plates. The culture is achieved in 175 µl of Neurobasal medium (GIBCO) complemented with final 1 mM of pyruvate and with B-27 1/100 (Beckton Dickinson). The cells are maintained in the culture for 6 days without changing the medium.

The treatments with the compounds to be tested are performed just after sowing at a final concentration of 3 µM in 0.5% dimethylsulfoxide (DMSO). Positive controls are made by adding BDNF (Brain-Derived Neurotrophic Factor) at 5 ng/ml (Tebu) finally. The negative controls only receive 0.5% DMSO.

Cell death is evaluated after 7 days by counting the number of living cells expressing GFP.

The activity of the compounds to be tested was evaluated by their capability of preventing death of striatum neurones grown in the Neurobasal medium, as compared with survival of striatum neurones in a medium supplemented with BDNF.

Results:

The obtained results are shown in the summary table located below.

The results are expressed as a ratio evaluating survival of positive GFP cells in the presence of the compound to be tested. This is therefore the number of living cells after treatment with the compound to be tested, reduced by the number of living cells after treatment with DMSO, based on (divided by) the number of survival cells after treatment with BDNF, reduced by the number of living cells after treatment with DMSO.

This ratio therefore represents the survival percentage due to the tested compound relatively to survival induced by BDNF.

In this test, a compound is considered as being active when said ratio is larger than 0.2 i.e. when it has a neuroprotective activity at least equal to 20% of the neuroprotective activity of BDNF.

TABLE 1

Table summarizing the pharmacological activities of the products of formula I

| Compound of Example No. | Concentration in µM | GFP ratio |
|---|---|---|
| 1 | 1 | >0.2 |
| 2 | 3 | >0.2 |
| 3 | 3 | >0.2 |
| 4 | 1 | >0.2 |
| 6 | 10 | >0.2 |
| 7 | 3 | >0.2 |
| 8 | 10 | >0.2 |
| 9 | 3 | >0.2 |
| 10 | 1 | >0.2 |
| 11 | 1 | >0.2 |
| 12 | 10 | >0.2 |
| 13 | 1 | >0.2 |
| 14 | 1 | >0.2 |
| 15 | 1 | >0.2 |
| 16 | 3 | >0.2 |
| 17 | 1 | >0.2 |
| 18 | 1 | >0.2 |
| 19 | 3 | >0.2 |
| 20 | 0.3 | >0.2 |
| 21 | 1 | >0.2 |
| 22 | 3 | >0.2 |
| 23 | 0.3 | >0.2 |
| 24 | 0.3 | >0.2 |
| 25 | 1 | >0.2 |
| 26 | 0.3 | >0.2 |
| 27 | 3 | >0.2 |
| 28 | 0.3 | >0.2 |
| 29 | 3 | >0.2 |
| 31* | 3 | >0.2 |
| 32** | 3 | >0.2 |

31* 3-phenyl-2-propenal-[4-(4-chlorophenyl)-2-thiazolyl]hydrazone; (Chembridge).
32** 3-phenyl-2-propenal-[4-(4-methylphenyl)-2-thiazolyl]hydrazone; (Chembridge).

Because of their neuroprotective effect, the compounds of formula I according to the invention therefore appear as good candidates for neuroprotective drugs, which may be used in treating neurodegenerative pathologies.

The invention claimed is:

1. A compound having the following formula I

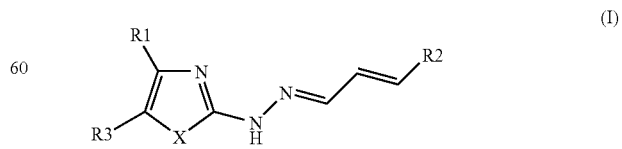

(I)

wherein

X represents sulfur;

R1 represents an aryl or heteroaryl group;

R2 represents an alkyl, cycloalkyl, aryl or heteroaryl group;
R3 represents a hydrogen atom,
with the exception of the compounds
3-phenyl-2-propenal-[4-(4-nitroxyphenyl)-2-thiazolyl]hydrazone;
3-phenyl-2-propenal-[4-(4-methoxyphenyl)-2-thiazolyl]hydrazone;
3-phenyl-2-propenal-[4-(4-fluorophenyl)-2-thiazolyl]hydrazone;
3-phenyl-2-propenal-[4-(4-bromophenyl)-2-thiazolyl]hydrazone;
3-phenyl-2-propenal-[4-(4-chlorophenyl)-2-thiazolyl]hydrazone;
3-phenyl-2-propenal-[4-(4-methylphenyl)-2-thiazolyl]hydrazone;
3-phenyl-2-propenal-[4-(1-naphthalenyl)-2-thiazolyl]hydrazone;
3-phenyl-2-propenal-[4-(2,4-dichlorophenyl)-2-thiazolyl]hydrazone;
3-phenyl-2-propenal-[4-(3-nitrophenyl)-2-thiazolyl]hydrazone;
2-butenal-[4-(4-nitrophenyl)-2-thiazolyl]hydrazone;
cinnamaldehyde-(4-phenyl-2-thiazolyl)hydrazone;
crotonaldehyde-(4-phenyl-2-thiazolyl)hydrazone;
as well as their addition salts with pharmaceutically acceptable acids.

2. The compound of formula I according to claim 1, characterized in that R1 is a phenyl radical substituted in the para position with a chlorine atom, with a methyl or trifluoromethyl group, or in the meta position with a hydroxyl or a phenyl group disubstituted in ortho position with a methoxy group and in para position with a chlorine atom, or in ortho position with a methyl group and in para position with a hydroxyl group, or in meta position with a fluorine atom and in para with a chlorine atom.

3. The compound of formula I according to claim 1, characterized in that R2 is a pyridin-4-yl, pyridin-2-yl or pyridin-3-yl group, or a benzo[1,3]dioxol5-yl group, or a phenyl group, or a phenyl group substituted in meta position with a nitro, cyano, methoxy, amino, methylsulfonyl, amide, methylketone, hydroxymethyl or hydroxyl group, or a phenyl group substituted in ortho position with a methoxy or a methyl group, or with a fluorine or chlorine atom, or a phenyl group substituted in para position with a fluorine atom.

4. The compound of formula I according to claim 1, characterized in that
R1 is a phenyl group substituted in the para position with a chlorine atom, a trifluoromethyl group, or in the meta position with a hydroxyl group, or a phenyl group, substituted in both ortho position with a methoxy group and in the para position with a chlorine atom, or substituted in both ortho position with a methyl group and in para with a hydroxyl group, or substituted in both meta position with a fluorine atom and in para with a chlorine atom;
R2 is a pyridin-4-yl, pyridin-2-yl or pyridin-3-yl radical, or a benzo[1,3]dioxol-5-yle radical, or a phenyl group, or a phenyl group substituted in meta position with a nitro, cyano, amino, methylsulfone, amide, methylketone, hydroxymethyl, hydroxyl or methoxy group, or a phenyl group substituted in ortho position with a methoxy group, a methyl group, or a fluorine or a chlorine atom, or a phenyl group substituted in para position with a fluorine atom.

5. The compound of formula I according to claim 1, acterized in that this is 3-(2-fluorophenyl)-2-propenal-[4-(4-chlorophenyl-2-thiazolyl)hydrazone;
3-(3-nitrophenyl)-2-propenal-[4-(4-chlorophenyl-2-thiazolyl)hydrazone;
3-(2-methoxyphenyl)-2-propenal-[4-(4-chlorophenyl-2-thiazolyl)hydrazone;
3-(3-methoxyphenyl)-2-propenal-[4-(4-chlorophenyl-2-thiazolyl)hydrazone;
3-phenyl-2-propenal-[4-(3-hydroxyphenyl-2-thiazolyl)hydrazone;
3-pyridin-4-yle-2-propenal-[4-(4-chlorophenyl-2-thiazolyl)hydrazone;
3-(2-methylphenyl)-2-propenal-[4-(4-chlorophenyl-2-thiazolyl)hydrazone;
3-(3-cyanophenyl)-2-propenal-[4-(4-chlorophenyl-2-thiazolyl)hydrazone;
3-(2-chlorophenyl)-2-propenal-[4-(4-chlorophenyl-2-thiazolyl)hydrazone;
3-(3-aminophenyl)-2-propenal-[4-(4-chlorophenyl-2-thiazolyl)hydrazone;
3-(3-nitrophenyl)-2-propenal-[4-(4-trifluoromethylphenyl-2-thiazolyl)hydrazone;
3-((E)-3-{[4-(4-chlorophenyl)-thiazol-2-yl]-hydrazono}-propenyl)-phenol;
3-pyridin-4-yl-2-propenal-[4-(4-trifluoromethylphenyl-2-thiazolyl)hydrazone;
3-(3-aminophenyl)-2-propenal-[4-(4-trifluoromethylphenyl-2-thiazolyl)hydrazone;
3-(3-methanesulfonylphenyl)-2-propenal-[4-(4-chlorophenyl-2-thiazolyl)hydrazone;
3-(3-cyanophenyl)-2-propenal-[4-(4-hydroxyphenyl-2-thiazolyl)hydrazone;
3-(3-benzo[1,3]dioxol-5-yl)-2-propenal-[4-(4-trifluoromethylphenyl-2-thiazolyl)hydrazone;
3-phenyl-2-propenal-[4-(4-chloro-2-methoxyphenyl-2-thiazolyl)hydrazone; —1-[3-((E)-3-{[4-(4-trifluoromethylphenyl)-thiazol-2-yl]-hydrazono}-propenyl)phenyl]-ethanone;
3-pyridin-2-yl-2-propenal-[4-(4-chlorophenyl-2-thiazolyl)hydrazone;
3-pyridin-2-yl-2-propenal-[4-(4-trifluoromethylphenyl-2-thiazolyl)hydrazone;
3-methyl-4-(2-{N'-[(E)-3-phenylprop-2-en-(E)-ylidene]-hydrazino}-thiazol-4-yl)-phenol;
[3-((E)-3-{[4-(4-trifluoromethylphenyl)-thiazol-2-yl]-hydrazono}-propenyl)phenyl]-methanol;
3-(4-fluorophenyl)-2-propenal-[4-(4-trifluoromethylphenyl-2-thiazolyl)hydrazone;
3-((E)-3-{[4-(4-trifluoromethylphenyl)-thiazol-2-yl]-hydrazono}-propenyl)benzamide; 3-phenyl-2-propenal-[4-(4-trifluoromethylphenyl)-2-thiazolyl]hydrazone; 3-((E)-3-{[4-(4-trifluoromethylphenyl)-thiazol-2-yl]-hydrazono}-propenyl)-phenol; 3-(3-methanesulfonylphenyl)-2-propenal-[4-(4-trifluoromethylphenyl-2-thiazolyl)hydrazone; and 3-(3-cyanophenyl)-2-propenal-[4(4-trifluoromethylphenyl-2-thiazolyl)hydrazone.

6. The compound of claim 1 wherein R2 is aryl or heteroaryl.

7. The compound of claim 1 wherein R2 is monocyclic aryl, aryl with a 1,3-dioxolyl substitution, or pyridinyl.

8. The compound of claim 1 wherein R2 is monocyclic aryl.

9. The compound of claim 1 wherein R2 is phenyl, substituted phenyl, or pyridinyl.

10. The compound of formula I according to claim 1, characterized in that this is 3-phenyl-2-propenal-[4-(4-trifluoromethylphenyl)-2-thiazolyl]hydrazone; 3-((E)-3-{[4-(4-trifluoromethylphenyl)-thiazol-2-yl]-hydrazono}-propenyl)-phenol; 3-(3-methanesulfonylphenyl)-2-propenal-[4-(4-trifluoromethylphenyl-2-thiazolyl)hydrazone; and 3-(3-cyanophenyl)-2-propenal-[4-(4-trifluoromethylphenyl-2-thiazolyl)hydrazone.

11. A pharmaceutical composition comprising at least one compound of claim 1 and a pharmaceutically acceptable excipient or carrier.

12. A method of treating a neurodegenerative pathology which comprises administering to a subject in need thereof a therapeutically effective amount of the composition of claim 11 wherein the neurodegenerative pathology is Huntington's disease.

13. A method of protecting neurons which comprises exposing the neurons to at least one neuroprotective compound of claim 1.

14. The method of claim 13 wherein the method is practiced in a subject who suffers from a neurodegenerative pathology.

15. The method of claim 14 wherein the pathology is a polyglutamine neurodegenerative pathology.

16. The method of claim 13 wherein the method is practiced in a subject who suffers from a pathology selected from the group consisting of Huntington's disease, spino-bulbar muscular atrophy, and spino-cerebellar athaxia.

17. The method of claim 13 wherein said method is practiced in a subject suffering from Huntington's disease.

18. The method of claim 13 in which the neurons are striatum neurons.

* * * * *

UNITED STATES PATENT AND TRADEMARK OFFICE
CERTIFICATE OF CORRECTION

PATENT NO.       : 8,691,854 B2
APPLICATION NO. : 11/994354
DATED            : April 8, 2014
INVENTOR(S)      : Chaimbault et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1202 days.

Signed and Sealed this

Twenty-ninth Day of September, 2015

Michelle K. Lee
*Director of the United States Patent and Trademark Office*